United States Patent
Giaquinta et al.

(10) Patent No.: US 6,758,951 B2
(45) Date of Patent: Jul. 6, 2004

(54) SYNTHESIS AND CHARACTERIZATION OF MATERIALS FOR ELECTROCHEMICAL CELLS

(75) Inventors: Daniel M. Giaquinta, Sunnyvale, CA (US); Alexander Gorer, San Jose, CA (US); Martin Devenney, Mountain View, CA (US); Sum Nguyen, Fremont, CA (US); Leonid Matsiev, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 85 days.

(21) Appl. No.: 09/975,707

(22) Filed: Oct. 11, 2001

(65) Prior Publication Data

US 2003/0070917 A1 Apr. 17, 2003

(51) Int. Cl.[7] ........................ C25D 17/16; C25B 9/02; G01N 27/26; G01N 27/07
(52) U.S. Cl. ........................ 204/267; 204/269
(58) Field of Search ................. 204/267, 269

(56) References Cited

U.S. PATENT DOCUMENTS

| | | | |
|---|---|---|---|
| 3,132,080 A | | 5/1964 | Cann |
| 4,850,899 A | * | 7/1989 | Maynard ................ 439/628 |
| 5,643,742 A | * | 7/1997 | Malin et al. ................ 435/29 |
| 5,985,356 A | | 11/1999 | Schultz et al. |
| 6,187,164 B1 | | 2/2001 | Warren et al. |
| 6,376,233 B1 | * | 4/2002 | Wolf et al. ............ 435/288.4 |
| 6,468,410 B1 | | 10/2002 | Donne |
| 6,468,806 B1 | | 10/2002 | McFarland et al. |
| 6,507,945 B1 | * | 1/2003 | Rust et al. ................ 717/103 |
| 2002/0025573 A1 | * | 2/2002 | Maher et al. ............ 435/287.1 |
| 2002/0092767 A1 | * | 7/2002 | Bjornson et al. ........... 204/451 |
| 2002/0128734 A1 | * | 9/2002 | Dorsett, Jr. ................ 700/73 |
| 2003/0113713 A1 | * | 6/2003 | Glezer et al. ................ 435/5 |

FOREIGN PATENT DOCUMENTS

| | | | |
|---|---|---|---|
| GB | 2386949 A | * 10/2003 | .......... G01N/27/07 |
| WO | WO 98/14641 | 4/1998 | |
| WO | WO 00/67086 | 11/2000 | |
| WO | WO 00/77279 | 12/2000 | |

* cited by examiner

*Primary Examiner*—Roy King
*Assistant Examiner*—Harry D Wilkins, III

(57) ABSTRACT

An apparatus including a basis that has a plurality of wells associated therewith for defining a plurality of electrochemical cells; at least two electrodes sealingly disposed in each electrochemical cell; and circuitry for providing an electrical connection between an electrical source and each said cell. A particularly preferred apparatus employs at least one printed circuit board secured to the base. In a preferred method, candidate materials are introduced into the apparatus and their respective performances are analyzed.

19 Claims, 4 Drawing Sheets

SYNTHESIS AND CHARACTERIZATION OF MATERIALS FOR ELECTROCHEMICAL CELLS

TECHNICAL FIELD

The present invention relates to the high throughput synthesis and characterization of materials for electrochemical cells.

BACKGROUND

The search for improved electrochemical performance has stimulated research into improved materials for use in such applications. One approach to such research is addressed in commonly owned U.S. Pat. No. 6,187,164 (Warren et al; issued Feb. 13, 2001), hereby incorporated by reference. Another approach is addressed in PCT WO 00/77279 (Published Dec. 21, 2000), also incorporated by reference. The advances achievable through the above disclosures have stimulated further investigation into the development of additional high throughput techniques for performing electrochemical performance research.

SUMMARY OF THE INVENTION

The present invention provides yet another attractive high-throughput approach to electrochemical performance research. The invention is premised upon the discovery of an improved apparatus and methodology for defining electrochemical cells, pursuant to which many different electrolyte materials, electrode materials, electrochemical additives, current densities, catalysts, or the like may be the subject of high-throughput experimentation. The present invention advantageously may be employed to synthesize libraries of materials, to characterize libraries of materials or both.

In general, the apparatus of the present invention includes a base including a plurality of wells associated therewith for defining a plurality of electrochemical cells; at least two electrodes sealingly disposed in each electrochemical cell; and circuitry for providing an electrical connection between an electrical source and each said cell. A particularly preferred apparatus employs at least one printed circuit board secured to the base. In a preferred method, candidate materials are introduced into the apparatus and their respective performances are analyzed.

DETAILED DESCRIPTION OF THE PREFERRED EMBODIMENT

Figure 1:
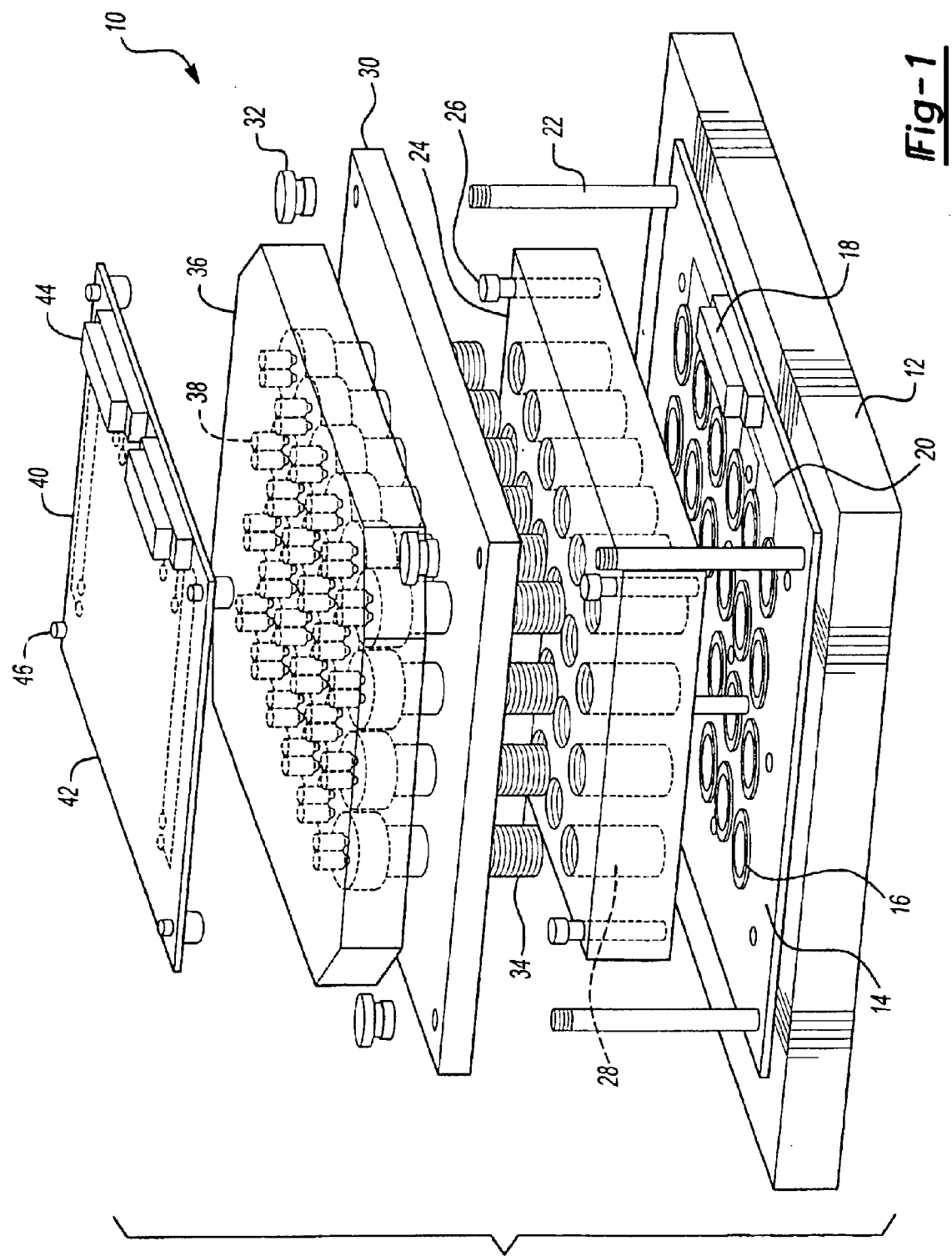
FIG. 1 is a perspective view of one illustrative apparatus in accordance with the present invention.

Referring first to FIG. 1, there is shown a system 10 of the present invention, which includes an electrochemical cell array for housing plural electrochemical cells on a common carrier. As will be seen the system is adapted for communication with an electrical source for applying electricity to each of the cells, for measuring responses within each cell to applied electricity or both. It will be appreciated that the preferred embodiment of the present invention is described in connection with a three-electrode system, namely a working electrode/counter electrode pair between which current is applied to maintain the desired voltage as measured between the working and a reference electrode. However, two electrode systems may also be employed, wherein the counter electrode may also serve as the reference electrode.

Accordingly, in a preferred embodiment, the system 10 includes a base 12 (which is optionally temperature controlled for heating or cooling over its entire surface or at specific regions or individual cell locations) for supporting an electrode assembly (e.g. a working electrode assembly) supported on a first printed circuit board, which is preferably a working electrode printed circuit board 14. In the preferred embodiment illustrated, the working electrode printed circuit board 14 includes a plurality of electrical conductors 16 (e.g., current collectors, electrodes or otherwise), which are in electrical communication with a suitable connector 18, such as by way of a conductive path or trace 20.

Optionally, the base includes appropriate hardware for aligning the various components and maintaining them in a desired position. For example, upright posts such as the illustrated threaded posts 22 may be provided, about or adjacent to which structures may be placed as desired. One such structure is a well plate 24 (itself possibly having like alignment posts 26), which includes at least one and more preferably a plurality of through holes formed therein, defining individually isolated passageways 28.

In one preferred embodiment, the walls defining the passageways 28 are threaded or are otherwise adapted for assisting in forming a fluid tight seal when the well plate is assembled with the printed circuit board for defining a plurality of electrochemical cells. Additionally, the apparatus may also include a middle plate 30, which may optionally incorporate or function as a sealing gasket. Caps 32 such as threaded fasteners may be provided as desired to aid in securing the assembly of components of the present apparatus.

In one preferred embodiment, a plurality of electrode holders 34 are provided. The holders preferably have an outside diameter approximating that of the passageways 28, and have a mating type configuration for engaging the walls of the passageway walls. For example, if the passageway walls are threaded, so will be the outer surface of the electrode holders 34. The electrode holders also preferably have an axial bore (preferably one that extends through substantially the entire length of the holder, shown more clearly as element 56 in FIG. 2), into or through which one or a plurality of electrodes may be placed. The holders may optionally omit a shoulder, so that the threaded portion extends substantially the entire length of the holder. A like structure is illustrated for example in PCT WO 00/77279 (Published Dec. 21, 2000).

Figure 2:
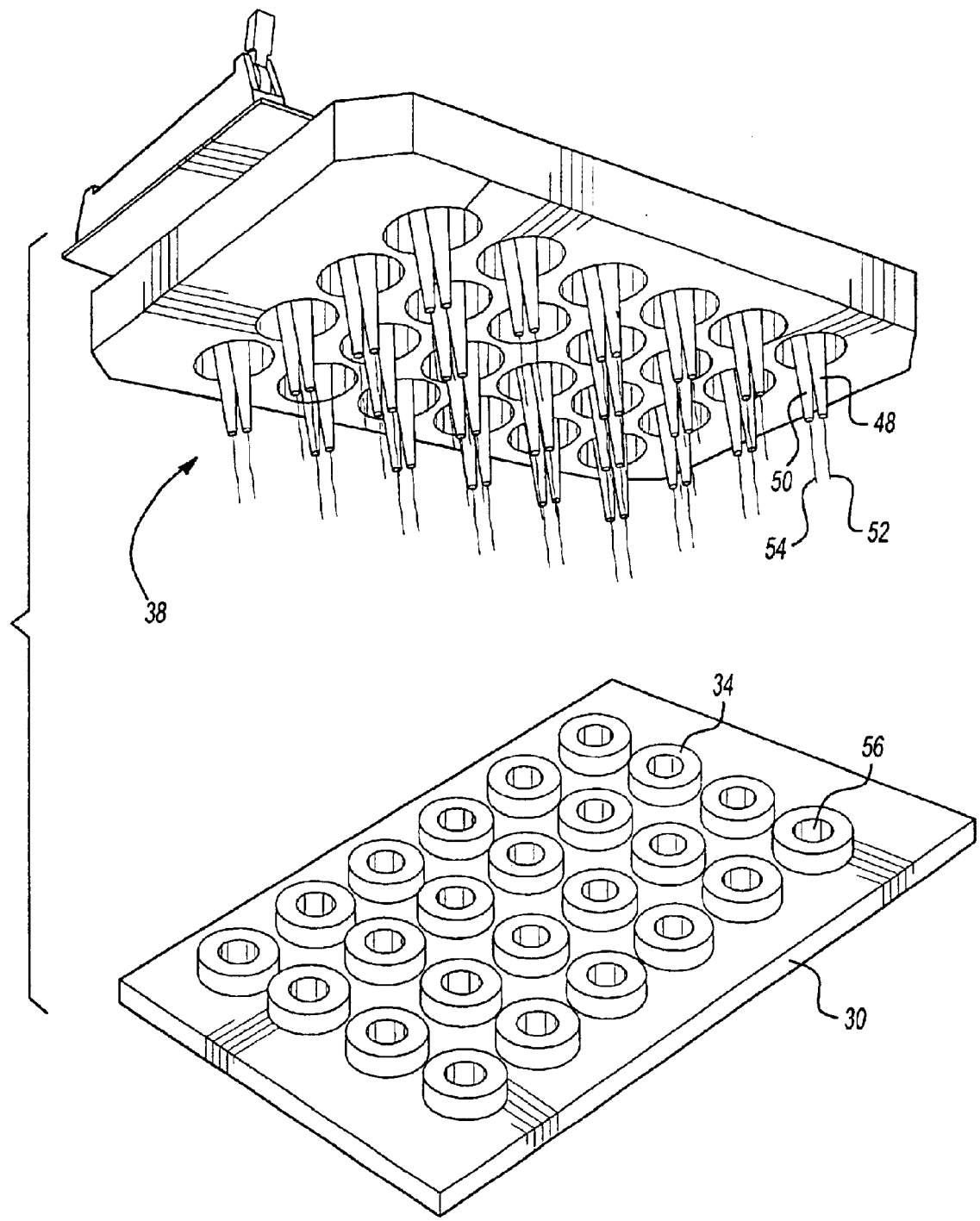
FIG. 2 is an exploded perspective view of a portion for carrying electrodes in accordance with the present invention.
Figure 3:
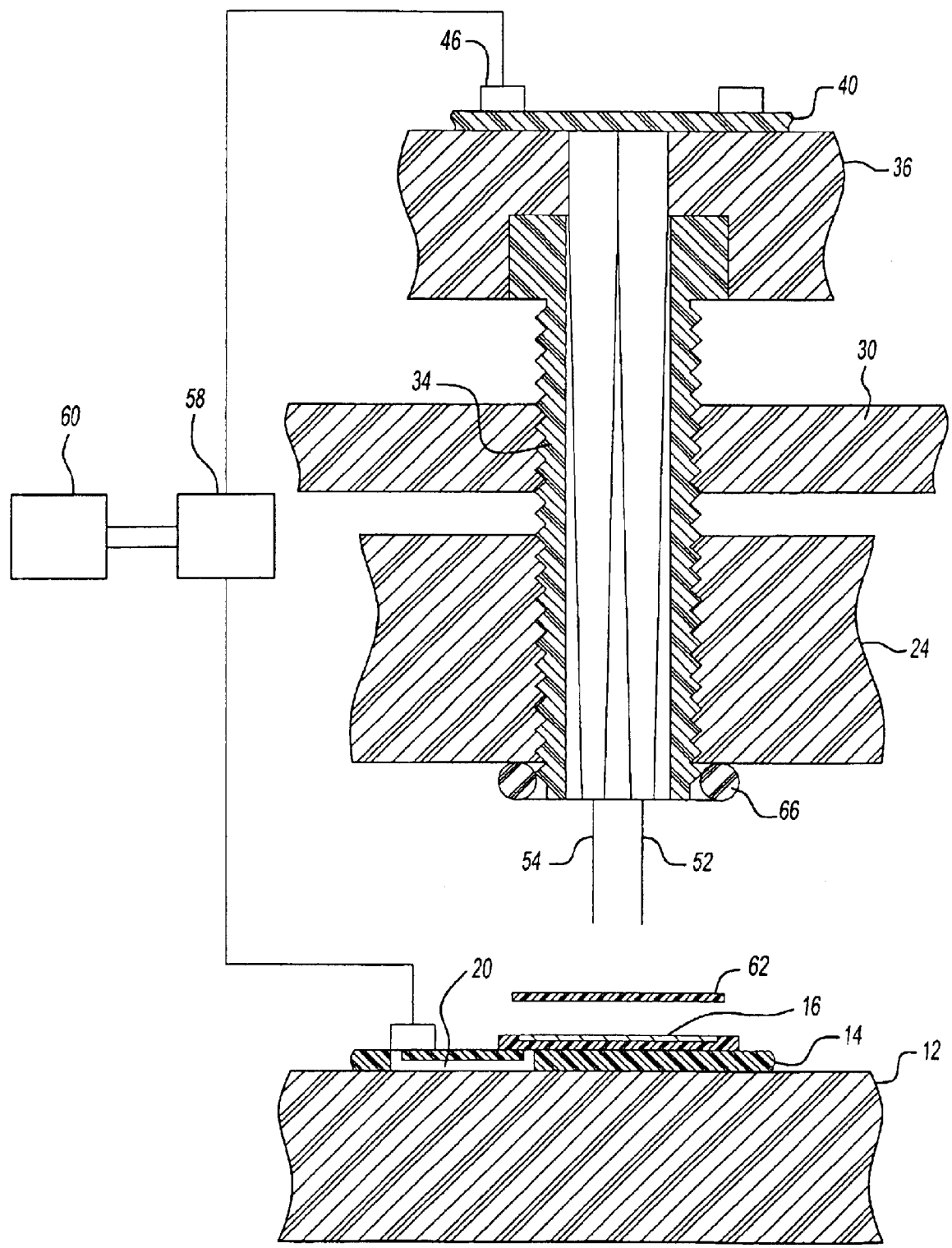
FIG. 3 is side sectional view of the apparatus of FIG. 1.

Electrodes are provided for extending at least partially into the axial bore 56. In one embodiment, the electrodes are configured so that they extend at least 25% the length of the holder, more preferably at least 45% the length and still more preferably at least 65% the length of the holder. The electrodes may be supported in any suitable manner within the axial bore. For instance an electrode support structure may be configured within the electrode holders 34. Alternatively, as illustrated in FIGS. 1–3, the electrodes are carried by a common carrier assembly 36, such as one defined on a substrate and optionally having a sheath assembly 38. The preferred embodiment employs a reference and a counter electrode as the electrodes carried by the carrier assembly 36. Of course, the electrodes may be varied so that a working electrode is carried by the carrier assembly or even a reference or working electrode associated instead with the working electrode printed circuit board 14.

A second printed circuit board 40 is also provided, and is adapted for communicating with electrodes carried by the carrier assembly 36. In the preferred embodiment illustrated the second printed circuit board includes a pattern 42 of contact pads and traces for allowing contact or other suitable electrical communication with and individual addressability of each of the individual electrodes. The pattern 42 in turn electrically communicates with suitable connectors, such as a multi-pin connector 44 for connection with an external power source. Suitable attachment devices 46 (e.g., threaded fasteners) may be employed for securing the second printed circuit board to the remainder of the assembly.

The first and second printed circuit boards of the present invention preferably are patterned and fabricated for defining a plurality of individually addressable electrodes on a common substrate, in the case of the working electrode printed circuit board, or a plurality of individually addressable contact pads on a common substrate in the case of the counter/reference electrode printed circuit board. Preferably the conductors or contact pads are electrically insulated relative to one another within the circuit board, but they need not be. Further, the conductors or contact pads may be integrally formed in the circuit board or may they be removably inserted therein (e.g., as disks).

The number of individual electrodes on the working electrode printed circuit board may vary from application to application, but preferably include at least two electrodes on a common substrate, more preferably at least 4 electrodes on a common substrate, and still more preferably at least 8 electrodes on a common substrate. One highly preferred embodiment employs at least 24 electrodes. Another highly preferred embodiment employs at least 48 electrodes, and yet another highly preferred embodiment employs at least 96 electrodes or more.

Likewise, the number of individual contact pads on the reference/counter electrode printed circuit board may vary from application to application, but preferably include at least two contact pads on a common substrate, more preferably at least 4 contact pads on a common substrate, and still more preferably at least 8 contact pads on a common substrate.

The electrodes may be substantially the same composition relative to each other or different. They may be substantially the same volume, thickness or dimension, or different. By way of example, illustrated herein are circular conductors 16. The shape may vary and may be polygonal or an irregular shape. The exposed area on the electrode preferably ranges from about 0.01 to about 1000 $cm^2$, more preferably from about 0.1 to about 50 $cm^2$, and still more preferably about 1 to about 10 $cm^2$. Further, while it is preferred for efficiency that a plurality of conductors are carried on a common substrate, it is also possible to employ plural substrates for carrying plural conductors.

In this regard, the volume of each of the respective resulting cells may vary from less than about 1 ml to greater than about 1 liter. Preferably, it ranges from about 0.1 ml to about 100 ml and more preferably about 1 ml to about 10 ml.

The substrate material may be any suitable material, and preferably it is a suitable dielectric or insulator material such as glass, silica, quartz, sapphire, alumina, magnesium oxide, silicon nitride, boron nitride, yttrium oxide, titanium dioxide, polyimide, hardened photoresist, plastics, or another suitable material known to be insulating in nature. Other suitable substrate materials will be readily apparent to those of skill in the art.

For the working electrode printed circuit board, the individual electrodes are connected to connector contact pads, preferably (but not necessarily) located adjacent edges of the substrate with suitable conductive traces. The electrodes, associated traces, and connector contact pads are fabricated from conducting materials (such as gold, silver, platinum, aluminum, copper, or other commonly used electrode materials). In like manner, for the reference/counter electrode printed circuit board, the individual electrode contact pads are connected to connector contact pads, preferably (but not necessarily) located adjacent edges of the substrate with suitable conductive traces.

Referring to FIG. 3, it can be seen that art-disclosed practices for lithographically patterning substrates may be employed for preparing the present circuit boards. By way of illustration, preferably a dielectric substrate is provided. Photolithographic techniques are applied to design and fabricate electrode or other conductor patterns on it. By applying a predetermined amount of photoresist to the substrate, photolyzing preselected regions of the photoresist, removing those regions that have been photolyzed (e.g., by using an appropriate developer), depositing one or more metals over the surface (e.g., by plating, CVD or PVD techniques such as sputtering, electron beam evaporation, pulsed laser deposition or the like) and removing predetermined regions of these metals (e.g., by etching, by dissolving the underlying photoresist, or the like), one can fabricate intricate patterns of individually addressable electrodes on the substrate.

Thereafter, a suitable connector (e.g., a multi-pin connector) can be affixed to the printed circuit board, with each pin in electrical communication with each of the individual connector contact pads. It may be also possible to omit the connector contact pads in favor of direct connection between the traces and the pins of the connector. Further, it may be desirable or possible that plural traces lead to a common junction upstream or downstream of the connector.

The connector may be placed in electrical communication with the potentiostat, galvanostat or both (collectively "potentiostat/galvanostat"), through the use of a suitable cable, wire bundles or other transmitter. For example a multi-wire ribbon cable may be employed.

As seen in FIGS. 1–3, electrodes carried by the electrode assembly may be carried in any suitable manner. However, preferably they are disposed in projecting relation relative to the second printed circuit board. They may project at any suitable angle. In one example, they project generally normal to the second printed circuit board 40. This may be accomplished in any suitable manner. Preferably the electrodes are supported by sheaths of the sheath assembly 38, such as a first sheath 48 and a second sheath 50 for a respective first electrode 52 (e.g., reference electrode) and a second electrode 54 (e.g., counter electrode). The sheaths are adapted for penetration into the passage 56 of the electrode holders. It can thus be seen how electrochemical cells are thereby formed.

As seen in FIG. 3, the respective connectors are in electrical or other signalling communication (optionally via an interface card 58, which may itself be integrated with one or both of the printed circuit boards or the like for addressably distinguishing between electrodes) with a suitable power source 60, such as a multi-channel potentiostat/galvanostat. Optionally, the interface card may be integrated with the power source. The power source may be any suitable power supply. Preferably it is an external power supply or a multi-channel potentiostat/galvanostat. It may also be a single channel instrument that is suitably multiplexed for individually addressing respective cells. Alternatively, it may be a collection of plural single channel or multi channel power sources each associated with one or a plurality of cells in the array.

It will be appreciated that the power source referred to herein as a potentiostat/galvanostat need not function as both a potentiostat and a galvanostat, but may function as one or the other. Further, it should be appreciated that references to "potentiostat" shall refer to a device for controlling the voltage that is applied across a working electrode/counter electrode pair. Thus, with reference to a three electrode set-up, voltage (and therefore current) is adjusted to maintain a potential difference between the working and reference electrodes. With reference to a two electrode mode (i.e., working and counter electrodes), a controlled potential difference is employed between the electrodes for allowing monitoring of any resulting current. A suitable feedback loop (e.g., a high impedance feedback loop) is employed for detecting such potential difference and adjusting for it. On the other hand, references to "galvanostat" refer to a device for controlling the current between a working electrode/counter electrode pair, allowing for instance monitoring of potential between the electrodes as a function of time (e.g., chronopotentiometry).

The multi-channel potentiostat/galvanostat is essentially a collection of individual potentiostats/galvanostats bundled together in a single unit. These individual potentiostats/galvanostats can precisely control the current or potential applied to each electrode in the system. In one illustrative embodiment, preferably any such potentiostat/galvanostat is capable of delivering at least 115 VAC (on the order of about 50 to about 60 HZ single phase) and about 500 VA max. Examples of suitable commercially available potentiostats/galvanostats include, without limitation, those available from Arbin Instruments under the BT-2000 product line (e.g., the BT-2043). The power source may be employed in the present invention for any art-disclosed technique for which it may be employed, including without limitation amperometric titration, electrogravimetry, coulometry, polarography, voltammetry, chronopotentiometry, or combinations thereof, including for example polarographic/voltammetric methods (such as single sweep, single step, triangular wave, cyclic or the like). Thus, the present invention contemplates using the disclosed arrays in the performance of one or more of the above techniques. It will also be appreciated that other instruments or analytical techniques may be employed such as for pH analysis using the arrays of the present invention.

As also seen in more detail in FIG. 3, the structure of the present invention allows for a variety of different types of experiments to be performed using the present apparatus. For example, though it is possible that the conductors 16 of the first printed circuit board can themselves function independently as an electrode, such as for electroplating (and thus may be formed of the same or different composition across the circuit board), it is possible that different samples of electrode compositions, additive compositions or the like may be placed within each electrochemical cell, with the conductors merely serving as current collectors. Thus, in one preferred embodiment, the conductors 16 are multi-functional. In another embodiment, they function primarily as a current collector. In yet another embodiment, they function primarily as an electrode.

Figure 4:
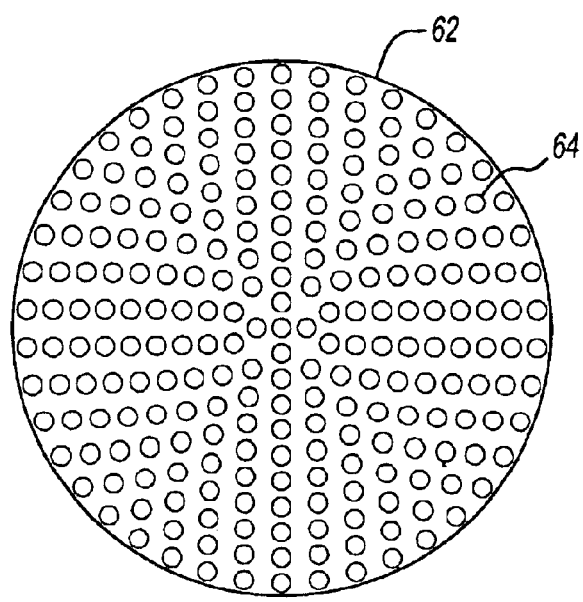
FIG. 4 is a plan view of one illustrative sample disk.
Figure 5:
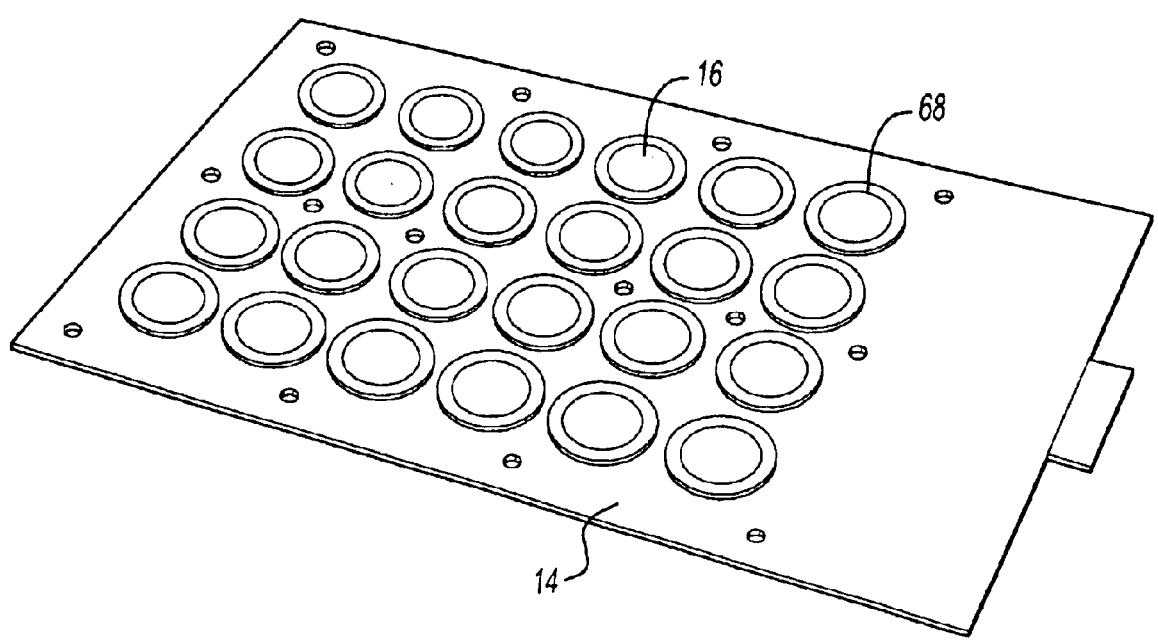
FIG. 5 is a plan view of a portion of an illustrative printed circuit board in accordance with the present invention.

If the conductors are intended to function primarily as a current collector, preferably the samples are supported on the conductors in a suitable manner. For instance, referring to FIGS. 3 and 4, for ease of re-use of the circuit board, optionally it is possible to use an inert spacer or like member, such as a disk 62 (e.g., a plastic member, such as a PTFE disk or the like), adapted for constraining sample materials such as powdered sample materials and allowing fluid communiction between the sample electrodes and the electrolyte. Thus, in a particularly preferred embodiment, the disk 62 is adapted for fluid passage therethrough, such as through apertures 64. Other support structures or porous members may be used as well such as screens, foams, wools, fabrics or the like. The sample may be further supported or constrained with a suitable frit, filter paper or the other suitable membrane structure on the disk 62. In such embodiments, and others, it is also desirable to include a suitable seal 66 for sealing each individual cell. The seal (e.g., an O-ring) may be provided on the well plate 24, the first printed circuit board 14, the electrode holders 34, the disk 62 or elsewhere. It may rest on or entirely enclose the disk 62 or the conductor 16. For instance, as illustrated in FIG. 5, a ridge 68, a trench or some other suitable structure may be formed on the printed circuit board for adapting it for sealing. The seal 66 may even be omitted in favor of such a structure, provided suitable sealing is possible.

Though other assembly configurations are possible, in one preferred embodiment, the first printed circuit board 14 is placed on the posts 22 over the base 12. O-ring seals 66 are placed in contact with the first printed circuit board 14. The well plate 24 is placed over the first printed circuit board so that the passageways 28 are aligned over the conductors 16. The plate 30 is placed into position and secured in place, thereby securing the well plate 24. If an electrode is to be analyzed in the cell, preferably it is loaded into the cell in a suitable form, such as a foil, or in powdered form (e.g., from about 1 nm to about 1000 microns, and more preferably about 1 to about 10 microns (e.g., about 5 microns)), and then compacted by pressure applied by electrode holder 34 to form a pellet that resides adjacent the first printed circuit board 14. Optionally, the application of pressure may be omitted. Thus, while substantially fully densified compaction is contemplated (e.g., greater than about 75% dense and more preferably greater than about 90% dense), it may also be undensified.

The electrode holders 34 are threaded into the passageways 28. Disks 62 and any associated membranes may be placed in the passageways before this step, and preferably after sample powder has been inserted. The leading ends of the electrode holders may then be threaded into the passageways for applying pressure to the disks directly, directly to the first printed circuit board (or any attendant intermediate structure such as a seal) or both. Thus, in a preferred embodiment, the electrode holders 34 may apply pressure to samples independently of other fasteners in the assembly. In this manner, it is possible to individually control the pressure applied by the electrode holder relative to the apparatus as a whole. In a preferred embodiment, the pressure applied by the electrode holder is applied directly to a powdered sample material.

The samples are desirably compacted by the application of pressure by the electrode holders 34 to the disks 62. Though higher or lower pressures may be employed, preferably about 0.1 to about 10 metric tons are applied per cell (e.g., for a time of from about 10 seconds to about 5 minutes or longer), and more preferably on the order of about 1 metric ton. The application of pressure thus effectively forms a pellet disposed within each cell for further experimentation.

The carrier assembly 38 and associated electrodes can then be placed in alignment over the appropriate cells along with the second printed circuit board 40, and secured in place if desired. Upon introduction of electrolytic fluid into each resulting cell and application of power from an external source it will be seen that an electrical circuit may be completed.

The above being a detailed review of one particularly preferred embodiment, it will be appreciated that any of a number of different modifications to the structure of the present system may be made, while remaining within the scope of the present invention. By way of example, it may be possible to omit the base 12 or the first printed circuit board 14, in favor of incorporating the function of the omitted element into the structure of the remaining element. It may be possible to omit the disks 62 entirely, or to integrally form like structures on the first printed circuit board 14, the well plate 24 the electrode holders 34, the sheaths 48, 50, or elsewhere. It is possible that plural supports (e.g., disks 62) are carried by a common substrate.

The dimensions of the resulting electrochemical cells may vary. For example, it is possible that the height of the cell is greater than, the same as or smaller than the diameter of the cell.

The electrode locations may be rearranged, e.g., substituting a reference or counter with a working electrode. Electrodes may be permanently or releasably attached to their respective printed circuit board. The printed circuit boards may by equipped with a mating type connector for attaching electrodes in electrical communication with the printed circuit boards. The functions of either of the printed circuit boards may be combined into the other for allowing a single board to be substituted for plural boards. It may also be possible to form one or more additional sensors for detecting additional properties of a material within the electrochemical cells, such as by the photolithographical formation of one or a plurality of sensors adjacent the cells on the printed circuit board or otherwise. One or more of the printed circuit boards or the intermediate structures may be formed with windows or other apertures therein for allowing viewing or other penetrating access to within the cells after assembly.

Seals may be formed integrally with the structure that is to be sealed, or provided as separate structures, such as rings, gaskets or the like. It might be possible to incorporate structure within any of the passageways, such as porous structures, constrictions, fluid paths, or the like.

The cells may be secured in place by other than threading engagement. For instance, there may be a ratchet/pawl attachment, friction fit (e.g. corking), snap fit, over center clamp, or the like. The electrodes may be permanently or releasably attached to a printed circuit board, and may be integrally formed thereon or secured mechanically, metallurgically (e.g., solder) or chemically (e.g., adhesive).

One or both of the printed circuit boards may be omitted in favor of other suitable hardware for forming an electrical circuit.

In one preferred embodiment, the printed circuit boards are re-useable for a plurality of experiments. In another embodiment, they are effectively disposable and are replaced after a single use for helping to assure experimental integrity.

Any suitable material may be employed. In one embodiment, a transparent plastic (e.g., acrylic), glass or the like is employed for the structure defining the individual cells for allowing reactions within cells to be visually monitored.

Each of the electrodes may be individually addressable (e.g., within their own respective circuits), or some or all of each of the respective working, counter or reference electrodes may be addressed in a single common circuit. Though a potentiostat/galvanostat is preferred, a plurality of individual power sources may be employed.

Each resulting electrochemical cell may be the same. Alternatively, the cells may vary from cell to cell in size, shape, materials, contents, temperature, pressure, power supply or otherwise. The cells may be arranged in a uniform pattern or a random pattern across an array.

The above steps may be varied in sequence, such as by assembling the entire apparatus before compacting the powder of the samples. The experiments performed may vary as well. For instance, in one embodiment, a common sample electrode material (e.g., same as to particle size, amount and composition) is employed in each cell and the electrolyte or electrolytic solution, dopants or other additives, current density, time, temperature, pressure, or the like is varied across the array of cells, with the resulting effects being measured, such as with the potentiostat. Conversely, it is possible that all conditions are kept equal and the particle size, amount or composition of sample electrode materials is varied across the array of cells. Variations in the compositions synthesized or analyzed may be obtained for example by varying electrode compositions, shape, dimension, volume or thickness, by varying the electrolyte (whether alkaline, acidic or neutral) introduced into the electrochemical cells, by varying the viscosity or form of the electrolyte (e.g., liquid, gel or the like), by changing the deposition technique used within a particular cell, such as by changing the deposition potential, changing the separator paper composition, coating or thickness, changing the length of the deposition time, varying the counter anions, using different concentrations of each species, and even using different electrochemical deposition programs (e.g., potentiostatic oxidation/reduction, galvanostatic oxidation/reduction, potential square-wave voltammetry, potential stair-step voltammetry, etc.). Other variations across an array may also be analyzed, such as temperature, cathode powder or electrolyte concentration, current density or the like. As to one of the specific illustrations herein, electrolytic manganese dioxide may be substituted with another compound, such as one or more different metal oxides, doped metal oxides or the like.

The system of the present invention can also be employed for performing each of the experiment types described in PCT WO 00/77279 (Published Dec. 21, 2000), incorporated by reference. Thus, current may be induced for causing electrochemical deposition of a material onto an electrode or current collector. An electrical response of a completed electrical circuit may be measured as well, such as for measuring performance of one or more of the samples or the effects of a particular variable.

The composition of electrodes may be varied. For instance, they may employ elements or compounds of elements selected from lanthanides and transition metals, such as La, Ce, Pr, Nd, Gd, Tb, Dy, Ho, Er, Tm, Y, Pm, Eu, Sm,Yb, Sc, Ti, V, Cr, Mn, Fe, Co, Ni, Cu, Zn, Y, Zr, Nb, Mo, Ru, Rh, Pd, Ag, Cd, Hf, Ta, W, Re, Os, Ir, Pt, Au, Hg, as well as other elements such as Al, Ga, Ge, In, Sn, Sb, Te, Tl, Pb, or Bi. Alternatively, art-disclosed compositions may be employed. For example, the reference electrode may be a standard reference electrode (such as Ag/AgCl, SHE, SCE, Hg/HgO, or $Hg/HgSO_4$) or a quasi-reference electrode (such as a piece of Pt wire).Though shown essentially as wires, the electrodes may be any suitable configuration, and preferably one having a relatively high surface area per unit volume. The present invention is also attractive for use in combinatorial programs involving rechargeable batteries, such as lithium batteries, nickel-cadmium batteries, nickel-metal hydride batteries, polymer batteries, or the like. Thus, suitable materials for these applications may be employed as desired.

In one particularly preferred embodiment, the present invention is employed for preparing and testing metal compounds, such metal salts or metal oxides for their efficacy in electrochemical cells. The metal compounds may be pure or they may be treated with additives or dopants (e.g., by adding salts to a plating bath). In a highly preferred embodiment, the present invention is used for experiments for preparing electrolytic manganese dioxide (EMD), such as by passing a current in a cell in the presence of manganese sulfate and sulfuric acid, and optionally in the presence of dopants or other additives.

In another application, as addressed elsewhere herein, the system of the present invention is used for co-precipitation of graphite and a cathode material. It will be appreciated that for enhancing conductivity within the powders (particularly for experiments for preparing cathode samples) of each cell, the powder may have graphite or another like material intermixed throughout. In one preferred embodiment, the graphite particle size and the sample electrode particle size preferably generally matches each other and will range from about 1 nm to about 100 microns, and more preferably about 1 to about 10 microns (e.g., about 5 microns). The amount of graphite to the powder electrode sample ranges from about 15:1 to about 1:15, more preferably about 9:1 to about 1:9, and more preferably is about 1:1.

It may also be possible to include additives other than graphite for reducing the amount of graphite without the need for increasing the amount or concentration of cathode material. Moreover, a suitable binder may also be employed. Preferably the apparatus of the present invention is employed for high throughput experimentation. Various approaches to such experimentation can be gleaned from commonly-owned U.S. Pat. Nos. 5,985,356 and 6,187,164, incorporated by reference herein. In one preferred embodiment, one or more of the steps is automated. For instance, Library Studio™ software, available from Symyx Technologies, may be used to design the libraries of experiments, see, U.S. patent application Ser. No. 09/174,856, filed Oct. 19, 1998 and U.S. patent application Ser. No. 09/420,334, filed Oct. 18, 1999, both of which are incorporated herein by reference for all purposes. This design software outputs a recipe file that can be interpreted by Impressionist™ software, from Symyx Technologies to create the libraries, as designed. For a description of the library synthesis software and its capabilities, see, U.S. patent application Ser. No. 09/305,830, filed May 5, 1999, and WO 00/67086, both of which are incorporated herein by reference for all purposes. Instruments can be controlled, data acquired, viewed and databased using Epoch™ software from Symyx Technologies, as discussed in U.S. patent application Ser. No. 09/550,549, filed Apr. 14, 2000, which is incorporated herein by reference for all purposes. The database to store and retrieve data can be based on Oracle® NT database, with other overlays, such as those disclosed in U.S. patent application Ser. No. 09/755,623, filed Jan. 5, 2001, which is incorporated herein by reference for all purposes.

Materials synthesized in accordance with the present invention can be characterized using any of a number of different types of art-disclosed characterization techniques. Solid materials may be analyzed for morphology, electrical properties, mechanical properties, chemical composition or the like. In one embodiment, the material is analyzed for at least two or more of morphology, electrical properties, mechanical properties, or chemical composition. In another embodiment, the material is analyzed for morphology, electrical properties, and chemical composition.

In one preferred embodiment, materials are analyzed using an art-disclosed beam-radiation technique. Examples of such analytical characterization techniques include, without limitation, x-ray photoelectron spectroscopy, x-ray diffraction, x-ray fluorescence, or the like.

In another preferred embodiment, the present invention is employed in a combinatorial materials research program. It will be appreciated that in connection with any combinatorial program, one approach for high throughput synthesis and analysis of materials is to employ varying compositions within a library or across a substrate. Examples of ratios and techniques for forming a variety of libraries are illustrated in U.S. patent application, Ser. No. 09/156,827 now abandon, entitled "Formation of Combinatorial Arrays of Materials Using Solution-Based Methodologies," hereby incorporated by reference.

Another aspect of the present invention involves correlating the data received from the test specimen analysis or other screen with information known about ingredients of each of the materials, processing conditions of each of the materials or a combination thereof. The respective test specimens of one or more libraries can be compared with each other based upon the data and ranked. In this manner, a large field of research candidates can be narrowed to a smaller field by identifying the candidates that perform better than others with respect to a predetermined property, structure, or figure of merit. Comparative review of results might lead to rankings of performance from better to worse, or the like. Likewise, a large field of research candidates can be narrowed to a smaller one by identifying those that meet a certain predetermined criteria. Additional libraries can then be prepared for further analysis. Alternatively, bulk quantities of materials having the desired properties or structures can be made for commercial applications. Data analysis may be performed manually, or by semi-automated or automated techniques. For example, it is possible to employ either or both of the LIBRARY STUDIO™(from Symyx Technologies,Inc.) and IMPRESSIONIST™(from Symyx Technologies,Inc.) for library design and synthesis, and POLYVIEW™(from Symyx Technologies,Inc.) or other suitable data management software to assist in correlating the data. Further, it is contemplated that data obtained from the use of the present invention can be used to develop data bases, such as a crystallography data base, or can be used for further interpretation or modeling.

It will be appreciated that the correlating protocol may be executed by suitable software. For instance, much of the above information typically will be inputted into a computer in the course of designing a library, (e.g. using software such as previously described LIBRARY STUDIO™), or in the course of programming or otherwise directing an instrument for exercising an operation upon a material (e.g. through the use of software such as IMPRESSIONIST™).

In this manner it is possible to store, retrieve, organize or otherwise manage information about many test specimens.

Further it is possible to analyze trends of different materials, or plural test specimens of the same material that has been subjected to different processing parameters or other conditions. An entire design space may be analyzed rapidly.

Preferably, the information is outputted for visual analysis. Trends can readily be analyzed within a single plot, or alternatively among different plots. In one embodiment, the plot may include only test specimens from a single library. In another embodiment the plot includes test specimens from different libraries.

Relative test specimen comparisons may be made for analyzing individual data points, or the data point may be confined to an analysis of whether a certain predetermined condition has been met. Materials may then be ranked according to the respective information known about them.

By way of illustration, suppose a library has five test specimens (or a multiple thereof). For illustration purposes, each test specimen is different from each other test specimen by the relative concentrations of their ingredients A and B (of course one or more other variables might be used instead of concentration) according to Table I.

| Test specimen | A | B | Crystalline (yes/no) | Electrical Property | Electrical Property Rank |
|---|---|---|---|---|---|
| 1 | 0 | 100 | No | 100 | 3 |
| 2 | 25 | 75 | No | 110 | 2 |
| 3 | 50 | 50 | Yes | 150 | 1 |
| 4 | 75 | 25 | Yes | 70 | 4 |
| 5 | 100 | 0 | No | 60 | 5 |

As can be seen, relative performance might be evaluated, as might be whether a predetermined criteria is satisfied, or possibly the specific quantitative data observed from the analysis.

It may also be possible to store the information about a library for future retrieval (e.g. more than one day, one week, one month, or even one year after characterization). Materials that do not meet a specified characteristic in the present may thereafter meet such specification. For example, referring to the Table I, it may be determined at some future date that a need exists for a blend of A and B that is crystalline but does not have an electrical property amount greater than 75. A query of a database including the information of Table I would identify Test specimen 4 as meeting this criteria. Information about the concentration or other parameters of Test specimen 4 could be retrieved and the material further analyzed.

Under any approach, it is also contemplated specifically that materials that satisfy certain criteria, perform better than others for a desired location or a combination thereof, can be identified for further study. Such further study might include further test specimen preparation and screening, the preparation of pilot- or bench-scale quantities or even the preparation of bulk quantities, (e.g. an amount sufficient to meet the demand of an industrial-scale application, for instance, such as a commercial application where the material is to be processed into useful commercially offered articles). Depending upon the intended application, a bulk quantity may be as small as 1 kg or less, but typically will be larger than about 10 kg, more preferably larger than about 100 kg and still more preferably larger than about 1000 kg and still more preferably greater than about 10,000 kg.

Throughputs obtainable according to the present invention preferably are high, and more preferably are higher than other art disclosed methods. Throughput will depend upon any of a number of different factors, including but not limited to the number of test specimens in a library, the size of the test specimens, the number of different characterizations performed upon given test specimens or the like. Assuming individual test specimen sizes less than 0.1 liter, in one highly preferred embodiment, a test specimen or library of test specimens is prepared and characterized for only one of morphology, size, physical property or mechanical property. Preferably test specimen preparation throughput averages no more than about 8 hours per test specimen, more preferably no more than about 4 hours per test specimen, still more preferably no more than about one hour per test specimen, and even still more preferably no more than about 0.25 hour per test specimen, and even still more preferably no more than about 0.1 hour per specimen. Additionally, extended duration tests (e.g., longer than one day, longer than one week or ever longer than one month) are also possible using the present invention, with one advantage of being able to test plural samples simultaneously.

EXAMPLE 1

About 100 mg of electrolytic manganese dioxide (EMD) is dispensed into each of 24 vials using an automatic solid handling robot. To each sample of EMD is added about 100 mg of graphite (Timcal, Ltd. KS6). About 22.0 $\mu$l 9M KOH is added to each EMD/graphite mixture. The resulting combination is finely ground and placed into each of the 24 cells of an electrochemical array as described in the above. The cathode powder is spread evenly in the cell and three layers of separator paper are placed on top of the powder. A porous Teflon disk is positioned on each cathode and 1 metric ton pressure is applied to each cathode for 45 seconds.

The assembly is assembled together and tightened, e.g. using a torque wrench (about 30 cm kg). About 3.1 ml 9 M KOH is added to each cell and with counter and reference electrodes in place, the array is allowed to equilibrate for at least about 30 minutes. The assembly is then connected electrically with a potentiostat and electricity is applied, with a different electrical condition applied to each of the respective cells.

EXAMPLE 2

Example 1 is repeated, but the composition of each of the cathodes is varied in the respective cells and electrical conditions are maintained substantially the same across the array.

EXAMPLE 3

Example 1 is repeated, but the electrolyte is varied in the respective cells and electrical conditions are maintained substantially the same across the array.

EXAMPLE 4

Example 1 is repeated, but the separator is varied in the respective cells and electrical conditions are maintained substantially the same across the array.

EXAMPLE 5

Example 1 is repeated, but the pressure is varied in the respective cells and electrical conditions are maintained substantially the same across the array.

EXAMPLE 6

Example 1 is repeated, but the temperature is varied in the respective cells and electrical conditions are maintained substantially the same across the array.

As should now be readily apparent, the present invention provides a superb method of electrochemically depositing, diverse materials, characterizing them or both. Using this invention, one can efficiently prepare libraries of varying elemental composition, and, since these libraries are prepared as including individually addressable cells, one can also directly measure properties of these materials. Using the present invention, it should be possible to synthesize and/or screen many new compositions at an unprecedented rate.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent application Ser. Nos. and publications, are incorporated herein by reference for all purposes.

What is claimed is:

1. An electrochemical cell apparatus, comprising:
   a) an assembly comprising a base, a printed circuit board supported on the base, and a well plate adjoining the printed circuit board, the well plate including a plurality of through holes defining individual isolated passageways in the well plate, the well plate and the printed circuit board being assembled with a fluid tight seal to define a plurality of electrochemical cells commonly supported by said base;
   b) at least two electrodes disposed in each of the plurality of electrochemical cells;
   c) the printed circuit board having defined thereon an individually addressable electrical communication path for electrically interfacing with each of said plurality of electrochemical cells; and
   d) circuitry for providing an electrical connection between an electrical source and one of said electrodes in each said cell via said printed circuit board.

2. The apparatus of claim 1, wherein said individually addressable electrical communication path includes a substantially circular metal conductor.

3. The apparatus of claim 1, wherein said printed circuit board is separately fabricated from said base.

4. The apparatus of claim 1, wherein a threaded assembly is employed for projecting disposition of electrodes into said well.

5. An electrochemical cell apparatus, comprising:
   a) a plurality of electrochemical cells commonly supported by a base;
   b) at least two electrodes, including a sample electrode, disposed in each of the plurality of electrochemical cells;
   c) an inert member in each of the plurality of electrochemical cells for constraining the sample electrode and allowing fluid communication between the sample electrode and an electrolyte, and
   d) a printed circuit board having defined thereon an individually addressable electrical communication path for electrically interfacing with each of said plurality of electrochemical cells; and
   e) circuitry for providing an electrical connection between an electrical source and one of said electrodes in each said cell via said printed circuit board.

6. The apparatus of claim 1 or 5, further comprising said electrical source and wherein said electrical source is a multi-channel potentiostat/galvanostat.

7. The apparatus of claim 1 or 5, wherein said electrodes include a working electrode and a counter electrode.

8. The apparatus of claim 7, further comprising a reference electrode.

9. The apparatus of claim 1 or 5, wherein the printed circuit board is first printed circuit board, the apparatus further comprising a second printed circuit board for contacting at least one of said electrodes in each of the plurality of electrochemical cells.

10. The apparatus of claim 9, wherein said first printed circuit board and said second printed circuit board are disposed in generally opposing relation to each other.

11. An electrochemical cell apparatus, comprising:
   a) an assembly comprising a base, a printed circuit board supported on the base, and a well plate adjoining the printed circuit board, the well plate including at least eight through holes defining individual isolated passageways in the well plate, each of the at least eight through holes having an associated first threaded portion, the well plate and the printed circuit board assembled with a fluid tight seal to define at least eight electrochemical cells commonly supported by said base;
   b) a sheath assembly having an associated second threaded portion for engaging said first threaded portion and projecting into each of said at least eight wells a first sheath and a second sheath, each having a longitudinal axis;
   c) a reference electrode in said first sheath for sealing disposition in each of the at least eight electrochemical cells generally in said axial direction;
   d) a counter electrode in said second sheath for sealing disposition in each of the at least eight electrochemical cells generally in said axial direction and generally parallel with said reference electrode;
   e) the printed circuit board having defined thereon an individually addressable electrical communication path, including individual traces electrically connecting with a working electrode corresponding to each of said at least eight wells for electrically interfacing with each of said at least electrochemical cells;
   f) a potentiostat/galvanostat; and
   g) circuitry for providing an electrical connection between said potentiostat/galvanostat and one of said electrodes in each said cell via said printed circuit board.

12. The apparatus of claim 11, wherein said potentiostat/galvanostat is a multi-channel potentiostat/galvanostat.

13. The apparatus of claim 11, wherein said traces originate at a multi-pin connector on said printed circuit board.

14. The apparatus of claim 13, wherein said circuitry connects to said multi-pin connector with a ribbon cable.

15. The apparatus of claim 11, wherein said longitudinal axes of each of said sheaths are generally parallel to each other.

16. The apparatus of claim 11, wherein said individually addressable electrical communication path includes a substantially circular metal conductor.

17. The apparatus of claim 11, further comprising a second printed circuit board for contacting at least one of said electrodes.

18. An electrochemical cell apparatus, comprising:
   a) an assembly comprising a base, a first printed circuit board supported on the base, and a well plate adjoining the first printed circuit board, the well plate including a plurality of through holes defining individual isolated passageways in the well plate, the well plate and the first printed circuit board being assembled with a fluid tight seal to define a plurality of electrochemical cells commonly supported by said base;

b) a first electrode sealingly disposed in each of the plurality of electrochemical cells, the first electrode being supported by the first printed circuit board, the first printed circuit board having defined thereon an individually addressable electrical communication path for electrically interfacing with the first electrode, and c) a second electrode sealingly disposed in each of the plurality of electrochemical cells, the second electrode being supported by a common carrier assembly having a sheath assembly, the sheath assembly allowing the second electrode to be projected into each of the plurality of electrochemical cells.

19. The apparatus of claim 18 further comprising a second printed circuit board supported by the common carrier assembly, the second printed circuit board having defined thereon an individually addressable electrical communication path for electrically interfacing with the second electrode.

* * * * *